US009486645B2

(12) United States Patent (10) Patent No.: US 9,486,645 B2
Wu et al. (45) Date of Patent: Nov. 8, 2016

(54) RADIATION THERAPY DEVICE FOR OCULAR MELANOMA

(71) Applicant: University of Miami, Miami, FL (US)

(72) Inventors: Xiaodong Wu, Miami, FL (US); Weizhao Zhao, Coral Gables, FL (US)

(73) Assignee: University of Miami, Miami, FL (US)

( * ) Notice: Subject to any disclaimer, the term of this patent is extended or adjusted under 35 U.S.C. 154(b) by 164 days.

(21) Appl. No.: 14/563,256

(22) Filed: Dec. 8, 2014

(65) Prior Publication Data

US 2015/0157879 A1 Jun. 11, 2015

Related U.S. Application Data

(60) Provisional application No. 61/913,678, filed on Dec. 9, 2013.

(51) Int. Cl.
*A61N 5/10* (2006.01)
*A61B 6/00* (2006.01)
*A61B 6/03* (2006.01)
*A61B 6/12* (2006.01)

(52) U.S. Cl.
CPC .......... *A61N 5/1037* (2013.01); *A61B 6/5247* (2013.01); *A61N 5/1017* (2013.01); *A61N 5/1067* (2013.01); *A61N 5/1084* (2013.01); *A61B 6/032* (2013.01); *A61B 6/12* (2013.01); *A61N 2005/1059* (2013.01)

(58) Field of Classification Search
CPC .. A61N 5/1017; A61B 6/032; A61B 6/5205; A61B 6/461; A61B 6/4233
See application file for complete search history.

(56) References Cited

U.S. PATENT DOCUMENTS 7,801,271 B2 * 9/2010 Gertner ................ A61N 5/1017
378/65
8,363,783 B2 * 1/2013 Gertner .................. A61B 3/113
351/206
2006/0176997 A1 * 8/2006 Dilmanian ........... A61N 5/1042
378/65

OTHER PUBLICATIONS

Abdel-Wahab et al.: "University of Miami Experience Using One Versus Two Intracavitary Brachytherapy Implants," Am J Clin Oncol (CCT) vol. 25, No. 3, 2002, pp. 313-317, Lippincott Williams & Wilkins, Inc., Philadelphia, consisting of 5 pages.
Abrams et al.: "Speed and Accuracy of Saccadic Eye Movements: Characteristics of Impulse Variability in the Oculomotor System," Journal of Experimental Physcology; Human Perception and Performance 1989, vol. 15, No. 3, pp. 529-543, American Psychological Association, Inc., consisting of 15 pages.
Brown et al.: "CyberKnife® Radiosurgery for Stage I Lung Cancer: Results at 36 Months," Clinical Lung Cancer, vol. 8, No. 8, pp. 488-492, 2007, consisting of 5 pages.

(Continued)

*Primary Examiner* — Hoon Song
(74) *Attorney, Agent, or Firm* — Christopher & Weisberg, P.A.

(57) ABSTRACT

The present invention advantageously provides a method and system for providing accurately localized, non-invasive radiation treatment for ocular melanoma or other intraocular indications through the completion of specified research tasks. The present invention further provides for dynamic localization of tumors associated with such indications. The system of the present invention includes the CYBERKNIFE system, a robust eye pupil tracking system, and an integrated software package to achieve intra-beam fractional tumor tracking during radiation delivery. The system may further include a mechanical phantom incorporated with a radiation dosimetry calibration kit for validation.

20 Claims, 11 Drawing Sheets

(56) References Cited

OTHER PUBLICATIONS

Brown et al.: "Early results of CyberKnife image-guided robotic stereotactic radiosurgery for treatment of lung tumors," Computer Aided Surgery, Sep. 2007, vol. 12, No. 5, pp. 253-261, consisting of 9 pages.
Carvounis et al.: "Gamma knife radiosurgery in neuro-ophthalmology," Curr Opin Ophtalmol 2003, vol. 14, pp. 317-324, Lippincott Williams & Wilkins, consisting of 8 pages.
Chang et al.: "A pre-operative approach of range of motion simulation and verification for femoroacetabular impingement," Int J Med Robotics Comput Assist Surg 2011, vol. 7, pp. 318-326, John Wiley & Sons, Ltd., consisting of 9 pages.
Chauvel et al.: "Proton therapy in ophthalmology: status report and problems encountered," Bull Cancer/Radiother 1996, vol. 83, Suppl. 1, pp. 215s-218s, Elsevier, Paris, consisting of 4 pages.
The Collaborative Ocular Melanoma Study Group: "The COMS Randomized Trial of Iodine 125 Brachytheraphy for Choroidal Melanoma, III: Initial Mortality Findings," COMS Report No. 18, pp. 969-982, American Medical Association, consisting of 14 pages.
The Collaborative Ocular Melanoma Study Group: "The COMS Randomized Trial of Iodine 125 Brachytheraphy for Choroidal Melanoma, II: Characteristics of Patients Enrolled and Not Enrolled," COMS Report No. 17, pp. 951-965, American Medical Association, consisting of 15 pages.
The Collaborative Ocular Melanoma Study Group: "The Collaborative Ocular Melanoma Study (COMS) Randomized Trial of I-125 Brachytherapy for Medium Choroidal Melanoma, I. Visual Acuity After 3 Years," COMS Report No. 16, pp. 348-366, American Academy of Ophthalmology, Elsevier Science, Inc., consisting of 19 pages.
The Collaborative Ocular Melanoma Study Group: "Assessment of Metastatic Disease Status at Death in 435 Patients With Large Choroidal Melanoma in the Collaborative Ocular Melanoma Study (COMS)," COMS Report No. 15, pp. 670-676, American Medical Association, consisting of 7 pages.
The Collaborative Ocular Melanoma Study Group: "Cause-Specific Mortality Coding: Methods in the Collaborative Ocular Melanoma Study," COMS Report No. 14, Controlled Clinical Trials, vol. 22, pp. 248-262, 2001 Elsevier Science, Inc., consisting of 15 pages.
The Collaborative Ocular Melanoma Study Group: "Consistency of observations from echograms made centrally in the Collaborative Ocular Melanoma Study," COMS Report No. 13, Ophthamic Epidemiology 2002, vol. 9, No. 1, pp. 11-27, Swets & Zeitlinger 2001, consisting of 18 pages.
The Collaborative Ocular Melanoma Study Group: "Echography (Ultrasound) Procedures for the Collaborative Ocular Melanoma Study (COMS), Report No. 12, Part I," J Ophth Nurs Technol, vol. 18, No. 4, Jul./Aug. 1999, pp. 143-149, consisting of 7 pages.
The Collaborative Ocular Melanoma Study Group: "Echography (Ultrasound) Procedures for the Collaborative Ocular Melanoma Study (COMS), Report No. 12, Part II," J Ophth Nurs Technol, vol. 18, No. 5, Sep./Oct. 1999, pp. 219-232, consisting of 14 pages.
The Collaborative Ocular Melanoma Study Group: "The Collaborative Ocular Melanoma Study (COMS) randomized trial of pre-enucleation radiation of large choroidal melanoma, III: Local complications and observations following enucleation," COMS Report No. 11, Am J Ophthalmol 1998, vol. 126, pp. 362-372, consisting of 10 pages.
The Collaborative Ocular Melanoma Study Group: "The Collaborative Ocular Melanoma Study (COMS) randomized trial of pre-enucleation radiation of large choroidal melanoma II: Initial Mortality Findings," COMS Report No. 10, Am J Ophthalmol 1998, vol. 125, No. 6, pp. 779-796, Elsevier Science, Inc., consisting of 18 pages.
The Collaborative Ocular Melanoma Study Group: "The Collaborative Ocular Melanoma Study (COMS) randomized trial of pre-enucleation radiation of large choroidal melanoma I: Characteristics of Patients enrolled and Not Enrolled," COMS Report No. 9, Am J Ophthalmol 1998, vol. 125, No. 6, pp. 768-778, Elsevier Science, Inc., consisting of 12 pages.
The Collaborative Ocular Melanoma Study Group: "Sociodemographic and Clinical Predictors of Participation in Two Randomized Trials: Findings from the Collaborative Ocular Melanoma Study," COMS Report No. 7, Controlled Clinical Trials, vol. 22, pp. 526-537, 2001 Elsevier Science, Inc., consisting of 12 pages.
The Collaborative Ocular Melanoma Study Group: "Histopathologic Characteristics of Uveal Melanomas in Eyes Enucleated From the Collaborative Ocular Melanoma Study," COMS Report No. 6, American Journal of Ophthalmology, vol. 125, pp. 745-766, 1998 Elsevier Science, Inc., consisting of 22 pages.
The Collaborative Ocular Melanoma Study Group: "Factors Predictive of Growth and Treatment of Small Choroidal Melanoma," COMS Report No. 5, Arch Ophthalmol., vol. 115, 1997, pp. 1537-1544, consisting of 8 pages.
The Collaborative Ocular Melanoma Study Group: "Mortality in Patients with Small Choroidal Melanoma," COMS Report No. 4, Arch Ophthalmol., vol. 115, Jul. 1997, pp. 886-893, consisting of 8 pages.
The Collaborative Ocular Melanoma Study Group: "Design and Methods of a Clinical Trial for a Rare Condition: The Collaborative Ocular Melanoma Study," COMS Report No. 3, Controlled Clinical Trials, vol. 14, pp. 362-391, Elsevier Science Publishing, Co., Inc. 1993, consisting of 30 pages.
The Collaborative Ocular Melanoma Study Group: "Complications of Enucleation Surgery," COMS Report No. 2, Retine and Vitreous, pp. 181-190, Symposium on Retina and Vitreous, organized by the New Orleans Academy of Ophthalmology, Mar. 12-15, 1992, 1993 Kugler Publications, Amsterdam / New York, consisting of 10 pages.
The Collaborative Ocular Melanoma Study Group: "Accuracy of Diagnosis of Choroidal Melanomas in the Collaborative Ocular Melanoma Study," COMS Report No. 1, Arch Opthalmol, vol. 108, Sep. 1990, pp. 1268-1273, consisting of 6 pages.
Damato et al.: "Proton Beam Radiotherapy of Choroidal Melanoma: the Liverpool-Clatterbridge Experience," Int. J. Raditaion Oncology Biol. Phys., vol. 62, No. 5, 2005, pp. 1405-1411, 2005 Elsevier Inc., consisting of 7 pages.
Dieterich et al.: "Report of AAPM TG 135: Quality assurance for robotic radiosurgery," Med. Phys. vol. 38, No. 6, 2011 Am. Assoc. Phys. Med., consisting of 23 pages.
Dikshit et al.: "An online interactive simulation system for medical imaging education," Computerized Medical Imaging and Graphics, vol. 29 (2005), pp. 395-404, Elsevier Ltd., consisting of 10 pages.
Emara et al.: "Sterotactic Radiotherapy in the treatment of Juxtapapillary Choroidal Melanoma: Preliminary Results," Int. J. Radiation Oncology Biol. Phys., vol. 59, No. 1, pp. 94-100, 2004 Elsevier Inc., consisting of 7 pages.
John D. Enderle: "The Fast Eye Movement Control System," Biomedical Engineering Fundamentals, pp. 16-1-16-21, consisting of 21 pages.
Fürweger et al.: "Patient Motion and Targeting Accuracy in Robotic Spinal Radiosurgery: 260 Single-Fraction Fiducial_free Cases," Int. J. Radiation Oncology Biol. Phys., vol. 78, No. 3, pp. 937-945, 2010 Elsevier Inc., consisting of 9 pages.
The Collaborative Ocular Melanoma Study Group: "Clear Cell Differentiation in Choroidal Melanoma," COMS Report No. 8, Arch Ophthalmol., Jul. 1997, vol. 15, pp. 894-898, consisting of 5 pages.
Hui et al.: "Radioactive Plaque Therapy," pp. 51-68, Lippincott Williams & Wilkins, consisting of 18 pages.
Harbour et al.: "Intraoperative Echographic Localization of Iodine 125 Episcleral Radioactive Plaques for Posterior Uveal Melanoma," Retina, The Journal of Retinal and Vitreous Diseases, 1996, vol. 16, No. 2, pp. 129-134, consisting of 6 pages.
Hérault et al.: "Monte Carlo Simulation of a Protontheraphy Platform Devoted to Ocular Melanoma," Medical Physics, vol. 32, No. 4, Apr. 2005, pp. 910-919, 2005 Am. Assoc. Phys. Med., consisting of 11 pages.
Jampol et al.: "THe COMS Randomized Trial of Iodine 125 Brachytherapy for Choroidal Melanoma: IV. Local Treatment Failure and Enucleation in the First 5 Years after Brachytherapy."

(56) References Cited

OTHER PUBLICATIONS

COMS Report No. 19, Ophthalmology 2002, vol. 109, pp. 2197-2206, 2002 American Academy of Ophthalmology, consisting of 10 pages.
Jaywant et al.: "Stereotactic radiotherapy in the treatment of ocular melanoma: A noninvasive eye fixation aid and tracking system," Journal of Applied Clinical Medical Physics, vol. 4, No. 2, Spring 2003, pp. 156-161, 2003 Am. Coll. Med. Phys., consisting of 6 pages.
Keller et al.: "Experimental measurement of radiological penumbra associated with intermediate energy x-rays (1MV) and small radiosurgery field sizes," Medical Physics,vol. 34, No. 10, Oct. 2007, pp. 3996-4002, 2007 Am. Assoc. Phys. Med., consisting of 8 pages.
Li et al.: "A New Graphical Simulation Client-Server Application Based on GATE.," IEEE 2010, Nuclear Science Symposium and Medical Imaging Conference, Oct. 2010, consisting of 2 pages.
Li et al: "QGATE: An Educational Environment to Learn and Perform Nuclear Medicine Imaging Simulation with GATE," The Open Medical Imaging Journal, 2011, vol. 5, pp. 26-33, 2011 Bentham Open, consisting of 8 pages.
Liščák et al.: "Radiosurgery in Ocular Disorders: Clinical Applications," Radiosurgery and Pathological Fundamentals Prog Neurol Surg., Basel, Karger 2007, vol. 20, pp. 324-339, consisting of 17 pages.
Marchini et al.: "Stereptactoc Radiosurgery of Uveal Melanomas: Preliminary Results with Gamma Knife Treatment," Stereotect Funct Neurosurg 1995, Col. 64, Suppl. 1, pp. 72-79, 1995 S. Karger AG, Basel, consisting of 8 pages.
McCartney: "Pathology of Ocular Melanomas," British Medical Bulletin 1995, vol. 51, No. 3, pp. 678-693, The Bristish Council 1995, consisting of 16 pages.
The Collaborative Ocular Melanoma Study Group: "Development and Validation of Disease-Specific measures for Choroidal Melanoma," COMS-QOLS Report No. 2, (reprinted) Arch Ophthalmol, vol. 121, Jul. 2013, pp. 1010-1020, 2003 American Medical Association, consisting of 11 pages.
The Collaborative Ocular Melanoma Study Group: "Quality of Life After Iodine 125 Brachytherapy vs Enucleation for Choroidal Melanoma: 5-Year Results from the Collaborative Ocular Melanoma Study: COMS-QOLS Report No. 3," Arch Ophthalmol, vol. 124, Feb. 2006, pp. 226-238, consisting of 13 pages.
Michalec et al.: "Proton Radiotheraphy Facility for Ocular Tumors at the IFJ PAN in Karaków Poland," Applied Radiation and Isotopes, vol. 68 (2010), pp. 738-742, 2009 Elsevier Ltd., consisting of 5 pages.
Miralbell et al.: "Stereotactic Radiotherapy for Ocular Melanoma: Initial Experience Using Closed Eyes for Ocular Target Immobilization," Technology in Cancer Research and Treatment, vol. 6, No. 5, Oct. 2007, pp. 413-417, Adenine Press (2007), consisting of 5 pages.
Mozes et al.: "Three-dimmensional A-mode ultrasound calibration and registration for robotic orthopaedic knee surgery," The International Journal of Medical Robotics and Computer Assisted Surgery 2010, vol. 6, pp. 91-101, Published online Dec. 14, 2009 in Wiley InterScience, consisting of 11 pages.
Sobrin et al.: "Outcomes of Iodine 125 Plaque Radiotherapy after Initial Observation of Suspected Small Choroidal Melanomas: A Pilot Study," Ophthalmology 205, vol. 112, pp. 1777-1783, 2005 by the American Academy of Ophthalmology, Published by Elsevier, Inc., consisting of 7 pages.
Somani et al.: "Stereotactic radiotherapy in the treatment of juxtapapillary choroidal melanoma: 2-year follow up," Can J Ophthalmol, vol. 44, No. 1, 2009, pp. 61-65, consisting of 5 pages.
Tabandeh et al.: "Intraoperative Echographic Localization of Iodine-125 Episcleral Plaque for Brachytheraphy of Choroidal Melanoma," American Journal of Ophthalmology 2000, vol. 129, pp. 199-204, 2000 Elsevier Scient Inc., consisting of 6 pages.
The U.S. National Library of Medicine's Visible Human Project: Visible Human Data Set. http://vhnet.nlm.nih.gov/.
Wong et al.: Quantitative Measurement of CyberKnife Robotic Arm Steering, Technology in Cancer Research and Treatment, vol. 6, No. 6, Dec. 2007, pp. 589-594, Adenine Press 2007, consisting of 6 pages.
Woodburn et al.: "Preliminary experience in the treatment of choroidal melanoma with gamma knife radiosurgery," J Neurosurg, Suppl. 3, vol. 93, Dec. 2000, pp. 177-179, consisting of 3 pages.
Wowra et al.: "Radiosurgery for Spinal Malignant Tumors," Deutsches Ärzteblatt International 2009, vol. 106, No. 7, pp. 106-112, consisting of 8 pages.
Wu et al.: "A Universal Notched Episceral Plaque Set for Brachytherapy of Intraocular Tumors Adjacent to the OPtic Nerve," Cureus, vol. 2, No. 6, consisting of 11 pages.
Zehetmayer et al.: "Fractionated Stereotactic Radiotherapy with Linear Accelerator for Uveal Melanoma—Preliminary Vienna Results," Strahlenther Onkol 1999, vol. 175, Suppl. II, pp. 74-75, Urban & Voegel 1999, consisting of 2 pages.
Zorlu et al.: "Intial results of fractionated CyberKnife radiosurgery for uveal melanoma," J Neruooncol (2009), vol. 94. pp. 111-117, Springer Science+Business Media, LLC. 2009, consisting of 7 pages.
Zytkovicz et al.: "Peripheral dose in ocular treatments with CyberKnife and Gamma Knife radiosurgery compared ot proton radiotherapy," Physics in Medicine and Biology, vol. 52 (2007), pp. 5957-5971, IOP Publishing, consisting of 16 pages.

\* cited by examiner

| Error Analysis | | |
|---|---|---|
| Pixel | mm | mm |
| 4.25 | 0.1 | 0.087 |
| 21.24 | 0.5 | 0.435 |
| 42.48 | 1 | 0.870 |
| 84.96 | 2 | 1.743 |

RADIATION THERAPY DEVICE FOR OCULAR MELANOMA

CROSS-REFERENCE TO RELATED APPLICATION

This application is related to and claims priority to U.S. Provisional Patent Application Ser. No. 61/913,678, filed Dec. 9, 2013, entitled RADIATION THERAPY DEVICE FOR OCULAR MELANOMA, the entirety of which is incorporated herein by reference.

STATEMENT REGARDING FEDERALLY SPONSORED RESEARCH OR DEVELOPMENT n/a

FIELD OF THE INVENTION

The present invention advantageously provides a method and system for providing accurately localized, non-invasive radiation treatment for ocular melanoma or other intraocular indications through the completion of specified research tasks. The present invention further provides for dynamic localization of tumors associated with such indications.

BACKGROUND OF THE INVENTION

Ocular melanoma is the most common primary cancer of the eye. It occurs most often in lightly pigmented individuals with a median age of 55 years. However, it can occur in all races and at any age. One of the effective managements of ocular melanoma is an invasive localized radiation treatment, most commonly performed via radioactive plaque brachytherapy. The plaque is a small gold cover or shield device containing low energy radioactive seeds, and is inserted into a plastic carrier. The plaque is sutured to the wall of the eye (sclera) beneath the base of the tumor with the patient under local or general anesthesia. The typical irradiation time is three to four days. The plaque is removed surgically after the completion of treatment. Its effectiveness was demonstrated by the Collaborative Ocular Melanoma Study (COMS) in a clinical trial funded by the National Eye Institute of the National Institutes of Health. The study began in 1986 and was carried out in a multi-institution setting.

The success of brachytherapy inspired efforts of using focused external photon radiations, x-rays, or gamma rays for localized radiation delivery to ocular melanoma with less or non-invasiveness. The treatment delivery systems and methods resulting from these efforts include GAMMA KNIFE® (Elekta AB, Stockholm, Sweden), CYBERKNIFE® (Accuray Inc., Sunnyvale, Calif.), and other systems incorporating medical linear particle accelerators. The major challenge of such systems and techniques, however, is the control of the patient's unpredicted eye movement. Although stereotactic radiation treatment with external photon beams has been attempted, there is no generally available robust eye motion-tracking mechanism. Active control of eye movement requires some level of invasive procedure, such as supra- and infraorbital nerve blocking and tethering sutures to the periorbital tissue. While some investigators carried out their treatments without eye fixation or with peribulbar injection of lidocaine for eye movement control, the accuracy of treatment delivery is inevitably compromised due to un-accounted-for eye movement during treatment.

CYBERKNIFE is an image-guided robotic radiosurgery system developed in the early 1990s and has reached technical maturity in recent years. The system utilizes modern diagnostic image processing techniques that delineate treatment target volume and follows a focused radiation dose plan, subsequently used for guiding a light-weight medical linear accelerator to deliver radiation to the tumor. The linear accelerator of 6 MV x-rays is mounted on a high-performance robot. With an onboard image guiding system, consisting of kV x-ray stereotactic imager (XSI) and a motion monitoring system (SYNCHRONY®, Accuray Inc., Sunnyvale, Calif.), small beams of radiation can be directed to the treatment target from a wide range of angles with sub-millimeter accuracy. The focused radiation beams from multiple directions (typically 100 to 200 beams, each beam lasting several to tens of seconds) create a highly concentrated radiation dose distribution with the ablative dose covering the treatment target and with the surrounding normal tissues being minimally exposed. The SYNCHRONY system can generate a mathematical model that predicts the tumor motion by correlating it with an external optic motion monitoring system. The information of tumor motion is then fed through the integrated control system to guide the robot to follow the treatment target in real time. Currently, the CYBERKNIFE real-time motion tracking system can only manage a tumor's "regular" movement resulting from the periodic respiratory motion.

The CYBERKNIFE system may include a motion simulation phantom. The motion simulation phantom can generate program-controlled movements with various speeds and magnitudes, which may be tracked by the motion monitoring system SYNCHRONY. The tracking accuracy of CYBERKNIFE falls within 0.5 mm during a 10-minute test.

The treatment of intracranial targets with CYBERKNIFE involves a 6D skull tracking technique. Stereotactic x-ray images are acquired repeatedly prior to turning on each treatment beam, the location of the tumor is updated and the aiming of the radiation beam is then adjusted. This is adequately accurate given the fact that the patient's head is immobilized and the intracranial targets are generally stationary in relation to the skull. When treating an intra-ocular target, the situation becomes more complicated due to the motion of the eye. The only way to accurately, precisely, and safely delivery high doses of radiation to the intraocular tumors without invasive immobilization of the eye would be to redirect the radiation beams to the tumor's updated position with sufficient frequency. Given the CYBERKNIFE's flexible mobility and the system's real-time motion response and robust control, minute and swift motion compensation by the CYBERKNIFE robot during the treatment of ocular tumors is practically achievable.

It is desirable to provide a non-invasive approach that can provide accurately localized radiation treatment for ocular melanoma or other intraocular indications through the completion of specified research tasks. It is further desirable to provide a surrogate and its associated data transformation system such that the changed tumor position can be dynamically localized.

SUMMARY OF THE INVENTION

The present invention advantageously provides a method and system for providing accurately localized, non-invasive radiation treatment for ocular melanoma or other intraocular indications. Specifically, the present application provides a system and method for dynamic localization of intraocular tumors during radiation therapy. A system for non-invasively treating ocular melanoma may include a CT imaging system, the CT imaging system generating a series of 3D images of a patient's eye and a tumor within the eye; an optical imaging system, the optical imaging system generating a series of 2D images of a pupil of the patient's eye; a processor in communication with the CT imaging system and the optical imaging system programmed to correlate the pupil's 2D images with the tumor's 3D images to determine a location of the tumor relative to the pupil in each of a plurality of pupil locations; and a robotic arm in communication with the processor and configured to direct radiation beams toward the tumor, the direction of the beams being based at least in part on the correlations by the processor. The correlation between the pupil's 2D images and the tumor's 3D images is performed by the processor according to the equation:

$$T_i(S) = A(P_i(Se)) T_0(S)$$

where: $T_i(S)$ is the tumor's position within the patient's skull coordinate system; $T_0(S)$ is an initial position of the tumor within the patient's skull coordinate system; $P_i(Se)$ is the pupil's position within the patient's eye coordinate system; and A is a transformation that is a function of $P_i(Se)$. For example, the initial position of the tumor may be the position of the tumor when the eye is in a neutral position. The transformation A may be an affine transformation, such as a 3×4 affine transformation. The system may further include an x-ray imaging system. A new location of the tumor relative to the pupil when the eye moves is determined by the processor according to the equation:

$$T_{updated} = T_{current}(S) \times T_{HeadCT2\text{-}To\text{-}HeadCT1} \times T^{-1}_{HeadXSI\text{-}To\text{-}HeadCT1}$$
$$= A(P_{current}(Se)) T_0(S) \times T_{HeadCT2\text{-}To\text{-}HeadCT1} \times T^{-1}_{HeadXSI\text{-}To\text{-}HeadCT1}$$

where: $T_{updated}$ is the tumor's new position of the tumor relative to the pupil; $T_{current}(S)$ is tumor's new position within the patient's skull coordinate system; $T_{HeadCT2\text{-}To\text{-}HeadCT1}$ is a transformation based on a change in position of the patient's head between a second series of 3D images by the CT system and a first series of 3D images by the CT system; $T_{HeadXSI\text{-}To\text{-}HeadCT1}$ is a transformation based on a change in position of the patient's head between a position in an x-ray image of the patient's head by the x-ray imaging system and the position of the patient's head in the first series of 3D images by the CT system; $T_0(S)$ is an initial position of the tumor within the patient's skull coordinate system; $P_{current}(Se)$ is the pupil's current position within the patient's eye coordinate system; and A is a transformation that is a function of $P_{current}(Se)$. For example, the initial position of the tumor may be a position of the tumor when the eye is in a neutral position. The robotic arm may deliver radiation beams to the tumor a plurality of times during a treatment, and the correlation between the pupil's 2D images and the tumor's 3D images is performed between the deliveries of sequential radiation beams in order to direct the radiation beams toward the tumor each time the radiation each time the radiation beams are delivered. Additionally, the correlation between the pupil's 2D images and the tumor's 3D images may be performed during the delivery of radiation beams, and the delivery of radiation beams may be paused when the correlation determines the tumor's position is a distance from radiation beams that is greater than a threshold distance. For example, the threshold distance may be 1 mm. The optical imaging system may include a camera and a camera holder.

A system for non-invasively treating ocular melanoma may include: a first imaging system, the first imaging system generating a first 3D image of a patient's eye and a tumor within the eye when the eye is in a first position and generating a second 3D image of the patient's eye and the tumor within the eye when the eye is in a second position; a second imaging system, the second imaging system generating a first 2D image of a pupil of the patient's eye when the eye is in the first position and generating a second 2D image of the pupil of the patient's eye when the eye is in the second position; a processor in communication with the first and second imaging systems, the processor being programmed to correlate the first 3D image with the first 2D image and the second 3D image with the second 2D image; and a robotic arm in communication with the processor and configured to deliver radiation to the tumor when the eye is in the first location and the second location, the location of the tumor being based on the correlations between the 3D images and the 2D images. The location of the tumor when the eye is in the second position may be determined by the processor by the equation:

$$T_2(S) = A(P_2(Se)) T_1(S)$$

where: $T_2(S)$ is the tumor's position within the patient's skull coordinate system when the eye is in the second position; $T_1(S)$ is the tumor's position within the patient's skull coordinate system when the eye is in the first position; $P_2(Se)$ is the pupil's position within the patient's eye coordinate system when the eye is in the second position; and A is a transformation that is a function of $P_2(Se)$. The transformation A may be an affine transformation.

A method for performing radiosurgery for ocular melanoma may include: generating a first 3D image of an eye having a tumor with a first imaging system when the eye is in a first position; generating a first 2D image of a pupil of the eye with a second imaging system when the eye is in the first position; correlating the first 3D image to the first 2D image with a computer having a processor; determining a first 3D location of the tumor with the computer based on the correlation of the first 3D image to the first 2D image; delivering radiation to the tumor from a treatment device based on the correlation of the first 3D image to the first 2D image; generating a second 3D image of the eye with the first imaging system when the eye is in a second position; generating a second 2D image of the eye with the second imaging system when the eye is in a second position; correlating the second 3D image to the second 2D image with the computer; determining a second 3D location of the tumor with the computer based on the correlation of the second 3D image to the second 2D image; and delivering radiation to the tumor from the treatment device based on the correlation of the second 3D image to the second 2D image. The method may also include pausing the delivery of radiation when at least one of the correlation of the first 3D image to the first 2D image and the correlation of the second 3D image to the second 2D image determines the tumor's position is a distance from a radiation delivery site that is greater than a threshold distance. The first imaging system may be a computed tomography system or a magnetic resonance imaging system. The determination of the tumor's second location may be determined by the computer by the equation:

$$T_2(S) = A(P_2(Se)) T_1(S)$$

where: $T_2(S)$ is the tumor's position within the patient's skull coordinate system when the eye is in the second position; $T_1(S)$ is the tumor's position within the patient's skull coordinate system when the eye is in the first position; $P_2(Se)$ is the pupil's position within the patient's eye coordinate system when the eye is in the second position; and A is a transformation that is a function of $P_2(Se)$.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
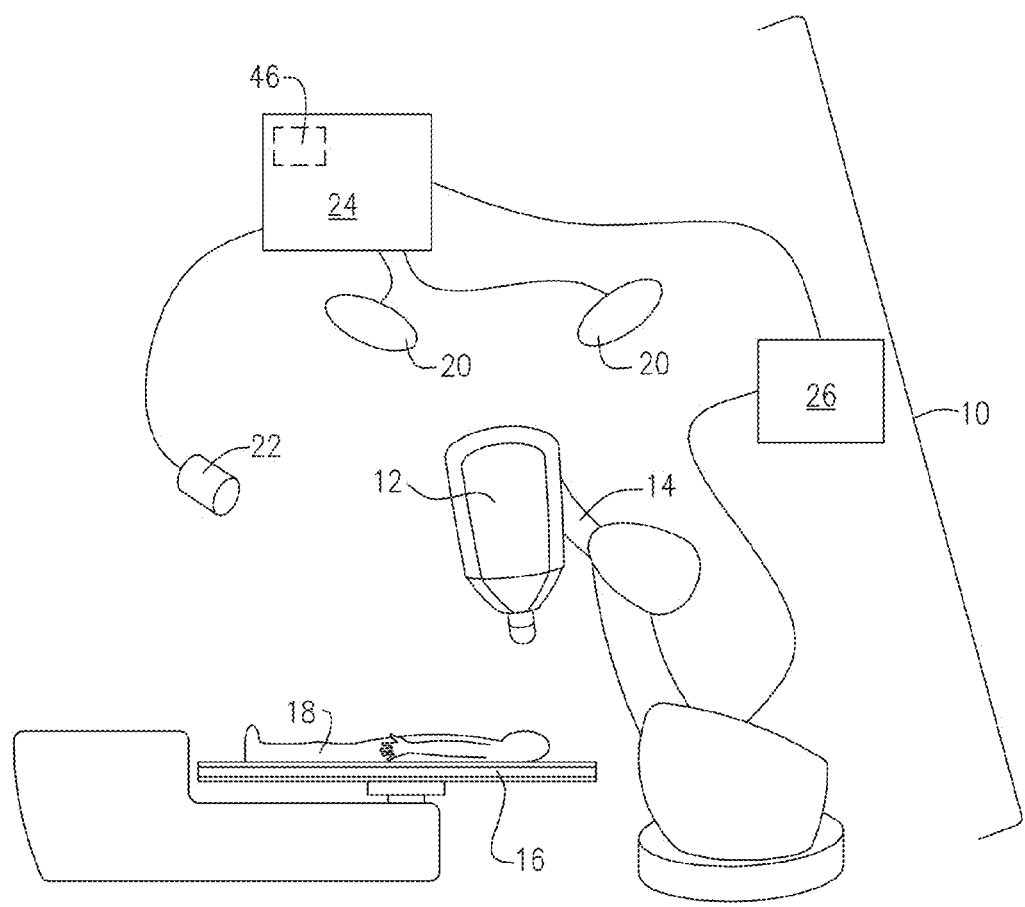
FIG. 1 shows a schematic view of a medical system in accordance with the present invention.

The present invention advantageously provides a method and system for providing accurately localized, non-invasive radiation treatment for ocular melanoma or other intraocular indications through the completion of specified research tasks. The present invention further provides for dynamic localization of tumors associated with such indications. The system of the present invention includes the CYBERKNIFE system, a robust eye pupil tracking system, and an integrated software package to achieve intra-beam fractional tumor tracking during radiation delivery. The system may further include a mechanical phantom incorporated with a radiation dosimetry calibration kit for validation. The present invention aims at three tasks: first, developing an ocular tumor motion tracking system through pupil tracking; second, integrating the pupil tracking system with the CYBERKNIFE system to realize intra-beam fractional tumor tracking during radiation delivery; and third, conducting a validation study and creating calibration procedures to further develop the system.

Non-invasive localized radiation treatment for ocular melanoma has been tested with the external photon machines including CYBERKNIFE. However, without real-time tracking of the eye motion, accuracy and precision would be compromised, affecting the clinical outcome. The present invention uses optic monitoring of the pupil centroid and, subsequently, through use of a data transformation system, provides the corresponding tumor location for radiation delivery. The proposed approach uses a commercial eye tracking system that provides the pupil's coordinates in real time. Additionally, a data transformation system is developed that correlates the pupil's coordinates and the tumor's coordinates to integrate the data transformation system with the CYBERKNIFE robotic control system together. Dosimetric validation is conducted, and reproducible pre- and intra-treatment calibration procedures are established. The developed communication software feeds the information to the CYBERKNIFE so that radiation beams can be actively adjusted and directed in short intervals to the tumor's updated position derived from the pupil's position. The proposed tracking method is innovative, reflected by the dynamic and feedback feature, as well as practically feasible. If systematically developed, the proposed approach would provide, for the first time, a complete solution to non-invasive radiosurgery of ocular melanoma or other ocular indications suitable for ablative radiation treatment, such as macular degeneration.

The same tracking system may also be applied to radiotherapy or radiosurgery of ocular tumors via proton and heavier charged particle beams. The unique position transformation software can be easily extended to determine not only the tumor location, but also the effective treatment depth. A scanning nozzle with dynamic energy adjustment would be necessary such that the location of the Bragg-peak (a pronounced peak on the Bragg curve which plots the energy loss of ionizing radiation during its travel through matter) can be adjusted in real time.

1. Experimental Data

A. CYBERKNIFE Application

Assurance of Accuracy

A schematic view of an exemplary medical system in accordance with the present invention is shown in FIG. 1. For example, the medical system 10 may include a CYBERKNIFE system with SYNCHRONY motion tracking system. For example, the system 10 may generally include a CYBERKNIFE device with a linear accelerator (LINAC) 12 mounted on a robotic arm 14, a treatment couch 16 on which a patient 18 may lie during treatment, one or more x-ray detectors 20, one or more cameras 22, one or more computers 24 for operating and receiving images and data from the one or more cameras 22, one or more x-ray detectors, and other system components. The system 10 may also include a console 26 for receiving user inputs, displaying system parameters and/or data to the user, and for controlling the operation of one or more other system components. However, it will be understood that the system 10 may include other components not shown or described herein.

Figure 2:
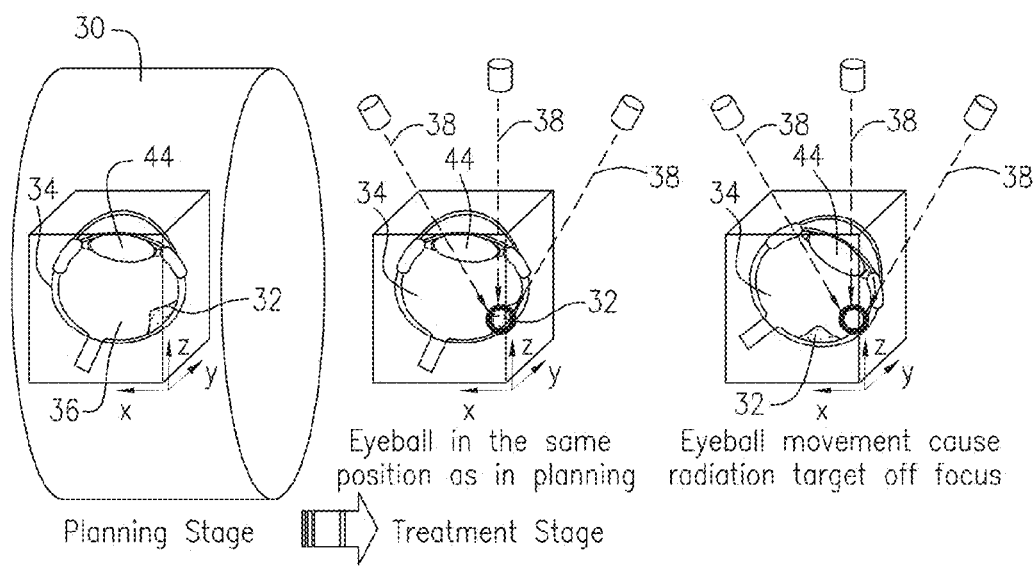
FIG. 2 shows a representation of the planning stage and treatment stage using a CYBERKNIFE system, with eyeball movement.

A representation of an exemplary CYBERKNIFE treatment method is shown in FIG. 2. A general radiosurgery procedure consists of two stages. In the planning stage, a computed tomography (CT) (or magnetic resonance imaging, MRI) 30 scan is conducted to localize a 3D position of a tumor 32 within an eyeball 34 with respect to the "CT space." Radiation dosimetry calculation is based on the 3D position of the tumor 32 and the 3D position of normal tissue 36 in the CT space. In the treatment stage, the patient's 3D position is registered by the x-ray stereotactic imager (XSI, a known technique) so that the CYBERKNIFE robotic arm 14 can be calibrated to recognize and follow the 3D information provided from the planning stage. When the tumor 32 moves in association with a predictable pattern, such as a tumor in the lung, the CYBERKNIFE uses a motion monitoring system (SYNCHRONY, a known technique) to dynamically adjust radiation beams 38, which may be aimed at the tumor 32 from multiple positions and angles, to follow the tumor's movement. In the case of ocular melanoma, however, the eyeball's movement is random and unpredictable. Therefore, SYNCHRONY does not work to adjust the CYBEKNIFE radiation beams to follow the tumor's movement. For example, as shown in FIG. 2, movement of the eye 34 may cause the radiation beams 38 to become off-target.

Figure 3:
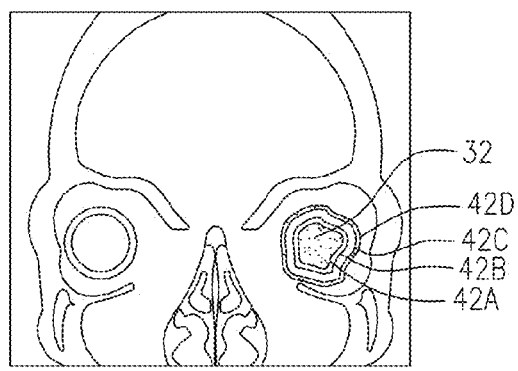
FIG. 3 shows an exemplary treatment plan.

A clinical study of radioactive eye plaques with 85 Grays (Gy) minimal tumor dose delivered in 3-5 days has shown 80%-97% of local intraocular control. Based on radiological calculation, this would be equivalent to 30 Gy-40 Gy delivered in a single fraction or 45 Gy to 60 Gy in three fractions. This estimate agrees with the studies conducted by other investigators. To evaluate the appropriateness of the CYBERKNIFE treatment for ocular melanoma, a number of test plans were created by using the CYBERKNIFE planning system. The test plans may include a number of radiation isodose lines 42A, 42B, 42C, 42D . . . surrounding the tumor 32, with a steep dose gradient (for example, as shown in FIG. 3). For example, the outermost isodose line 42D may be 30% of the prescribed radiation dose level covering the tumor 32.

B. CYBERKNIFE Response

Assurance of Dynamics

It is reasonable to assume that the primary eye motion of concern would be a saccadic mode. Such mode of eye movement, i.e. the trace of pupil 44 position, has been documented. A characteristic saccadic motion can reach a maximum velocity of hundreds of degrees per second. A saccadic motion of 40° (eyeball from center to left or right extreme position) is equivalent to a linear distance of 9 mm and takes about 0.1 s. If tracked accurately, the new tumor position caused by such motion can be easily intra-beam-updated and followed by the CYBERKNIFE's high-performance robot, which is capable to initiate motion with an acceleration of 1.5 g (gravitational acceleration).

2. Research Strategies

Figure 4:
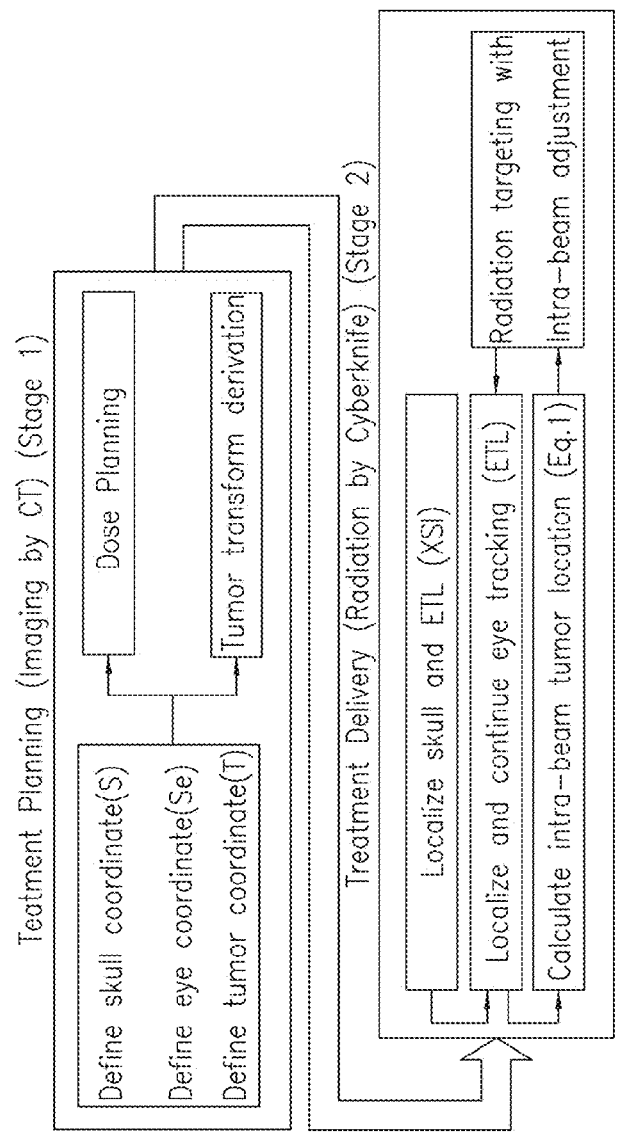
FIG. 4 shows a schematic image of the intra-beam eye-tracking treatment process.

Considering a relatively rigid relationship between eyeball and uveal melanoma, the innovation of the present invention lies in the integration of novel software, which correlates the eye motion with the tumor motion through transformations, with the subsequently controllable robotic arm, such that the radiation beams to the tumor can be adjusted with sufficient frequency. Skull fixation and localization may be achieved by the kv x-ray stereotactic imager (XSI), equipped with the CYBERKNIFE system, with a user-specified tracking frequency, typically every 10-20 seconds or 50-100 times throughout a treatment fraction. Based on this, the inventive system supplements with additional dynamic tracking of the eye movement and calibration procedure to assure the system's accuracy and precision. With the location of the tumor 32 defined by the CT (or MRI) in relation to both the skull and the eye, the tumor motion (i.e. a 3D transformation) can be precisely quantified. This quantified tumor's new position may then be used for robust radiation tracking. The present invention provides the final 40 Gy isodose line being better than 1 mm. An exemplary intra-beam eye-tracking treatment process is outlined in FIG. 4.

In the treatment planning stage (Stage 1), initial coordinates serving the dynamic tracking system may be obtained. For example, the skull coordinates (S), the eye coordinates (Se), and the tumor coordinates (T) may be defined, and the eye 34 may be tracked in Stage 1. The radiation dose may be planned using the initial coordinates. For example, a dose plan may be devised that includes a number of isodose lines 42 with a decreasing dose from the tumor 32 outward (for example, as shown in FIG. 3). The tumor transformation derivation may also be calculated in Stage 1.

In the treatment delivery stage (Stage 2), the tumor's position may be identified by eye-tracking between radiation beam application so as to update CYBERKNIFE's treatment plan for the next beam delivery. For example, the skull and an eye-tracking system device 50 (ETL) may be localized by the one or more x-ray detectors (XSI), the eyeball 34 may continue to be tracked by the eye-tracking system 50 (ETL), and the intra-beam tumor 32 location may be calculated according to Equations (1) and (2) (discussed below) in Stage 2. Between radiation beam delivery, the tumor's position may be identified by eye tracking so as to update the CYBERKNIFE's treatment plan for the next beam delivery. Within the period of a radiation beam delivery, the tumor's position may be monitored so as to control the delivered radiation's on/off condition (that is, whether radiation is being delivered or whether the radiation delivery is paused and/or the CYBERKNIFE device is turned off).

A. Eye Tracking System

Figure 5:
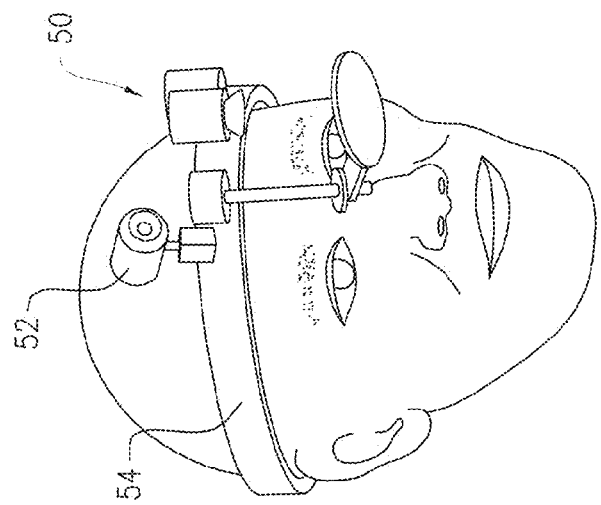
FIG. 5 shows the head-mounted Eye Tracking Lab (ETL) system for tracking eye movement.
Figure 6:
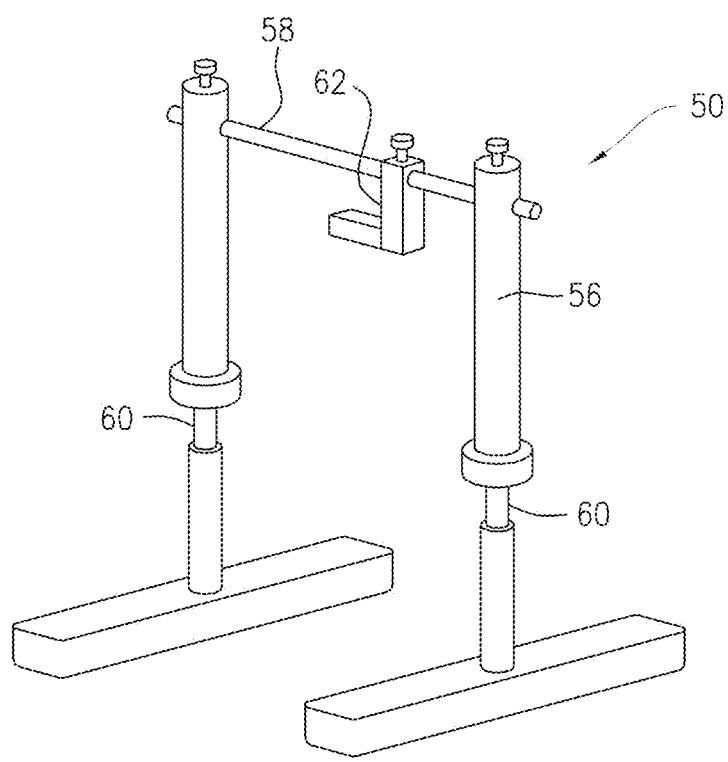
FIG. 6 shows a modified ETL system holder for tracking eye movement.

The system 10 may also include a head-mounted Eye Tracking Lab (ETL) 50 Model AA-ETL-101H, ISCAN, Inc., Woburn, Mass.) used for tracking eye movements. This system may track the pupil 44 movement in real time without restricting head movement (as shown in FIG. 5). The ETL system 50 may track the coordinates of the pupil 44 as it moves in the tracker-defined coordinate system (referred to as "ETL space"). The pupil's coordinate data from the ETL space will then be invariant to head position and may be used to streamline the process of tracking. The ETL 50 may include a camera 52 coupled to a holder 54 that is worn by the patient 18, in which case the pupil's coordinate may be determined by the "mounting" relationship between only the patient's head and the holder 54 worn by the patient 18. Alternatively, the holder may be modified to be a standalone device 56 (as shown in FIG. 6). Such a device 56 may be in a "Π" shape, with a central portion 58 mounted on the patient's head and leg portions 60 seated on a treatment couch 16, so that the ETL system may be repositioned across the patient's forehead during planning and treatment on the same position easily. Further, the device 56 may include an adjustable camera holder 62 and the height of each leg portion 60 may be adjustable. The target of the tracking system 50 may be the center of the pupil 44, so the pupil size is irrelevant. That is, the location of the center of the tracked pupil 44 is independent of lighting condition or patient's emotional status. The ETL's sampling frequency may be 60 Hz, which is about 20 ms/frame. This may allow each centroid coordinate to be updated in about 30 ms, considering integration of signal decoding, encoding, and transferring.

B. Tumor Localization and Tracking (Aim 1)

Figure 7:
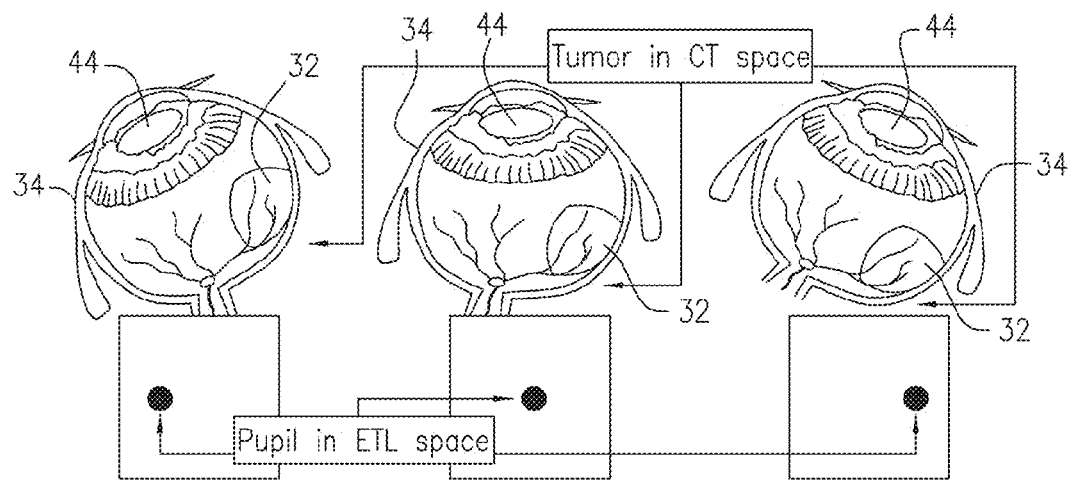
FIG. 7 shows an eye in various positions, and a schematic representation of the pupil positions corresponding to each eye position.

Tumor localization and tracking may occur at the planning stage, allowing for the acquisition of the pupil's 2D positions by the commercially available optic pupil motion monitoring device (Eye Tracking Lab, ETL) 50. A mathematical transformation may correlate the pupil's 2D position with the tumor's 3D position. During Stage 1, multiple series of thin-slice CT (or MRI) scans may be acquired. One series of CT scans may be used for treatment planning (CT1), and may be acquired with the eyeball in the neutral position (that is, with the patient looking straight ahead). The other CT series (CT2) may be acquired with the patient looking in the extreme upward, downward, right, and left directions. At the same time, the mounted ETL camera 52 may take pictures (optical images) of the patient's eye. These images, both CT (or MRI) and optical, correspond to the "extreme" corners allowed by eye movement. FIG. 7 shows the pupil 44 at a neutral position (center image of the figure), a first position (left image of the figure), and a second position (right image of the figure), and schematic representations of the corresponding pupil positions. However, other eye positions may also be tracked. The images acquired by the ETL 50 of the pupil positions in the ETL space may be correlated to the respective images in the CT acquisition series. By interpolation or analytical manipulation, a relationship between the pupil's 2D coordinates and the tumor's 3D positions can be established.

Let CT(i) denote the CT series of the eye position at the pupil 44 position i, with i=0 being the neutral position, when the tumor 32 is delineated. The pupil positions may be recorded by the ETL respectively as $P_i$, with i=0, 1, 2, 3 . . . n. Typically, n=4 for the eye's "extreme" directions, such as the top left, top right, bottom left, and bottom right. Let S denote the skull coordinate system (i.e. the CT 3D space) and Se denote the eye coordinate system (i.e. the ETL 2D space). The neutral coordinate of the tumor 32 in S may be specified as $T_0(S)$ and its corresponding pupil's coordinate in Se is $P_0(Se)$. By a series of CT scans, for example, five eye positions including the neutral position and four others, the tumor's locations and the pupil's coordinates can be expressed by Equation (1) below:

$$T_i(S)=A(P_i(Se))T_0(S) \quad (1)$$

where A is the transformation derived from the corresponding image series CT(i) and the pupil coordinate $P_i$. A is the function of pupil's $i^{th}$ position (that is, $P_i(Se)$ in the ETL space), and typically may be a 3×4 affine transformation matrix including rotation and translation information. A may be generated from the sparsely sampled data (for example, five positions) and be able to link all of the pupil's coordinates in the ETL space to the tumor's coordinate in the CT 3D space. A procedure may be developed that can generate the optimal transformations. Since the pupil positions may be acquired during Stage 1, the transformations may be determined prior to treatment.

C. System Integration and Adjustment (Aim 2)

An intra-treatment calibration procedure may be performed at the patient's treatment stage for system integration. For example, the one or more processors 46 may be programmed to execute an algorithm based on Equations (1) and (2) (discussed below). The procedure may enable communication and adjustment between the optic pupil motion monitoring system, the CYBERKNIFE system, and its associated x-ray stereotactic imager 20, such that the intra-beam fractional tumor coordinates can be transferred to the CYBERKNIFE robot and the radiation beam 38 can be adjusted to aim at the tumor's updated position. In order to deliver radiation beams 38 to the patient 18 exactly following the treatment plan, the CYBERKNIFE system may use the kv x-ray stereotactic images (XSI) to identify the patient's current position so that the patient's current position can be related to the planning position by a transformation $T_{HeadXSI\text{-}To\text{-}HeadCT1}$. There should be no displacement during the CT1 and CT2 scans. However, the relationship between the CT1 and CT2 data sets may be determined by $T_{HeadCT2\text{-}To\text{-}HeadCT1}$. For example, $T_{HeadCT2\text{-}To\text{-}HeadCT1}$ may be an identity matrix. As described above, the tumor's coordinate may be determined by $T_i(S) = A(P_i(Se))T_0(S)$. Thus, the tumor's updated position may be calculated using Equation (2) below:

$$T_{updated} = T_{current}(S) \times T_{HeadCT2\text{-}To\text{-}HeadCT1} \times T^{-1}_{HeadXSI\text{-}To\text{-}HeadCT1} \quad (2)$$

$$= A(P_{current}(Se))T_0(S) \times T_{HeadCT2\text{-}To\text{-}HeadCT1} \times T^{-1}_{HeadXSI\text{-}To\text{-}HeadCT1}$$

where the transformation A is determined by the pupil's current position, $P_{current}(Se)$ in the ETL space. $P_{current}(Se)$ is an unknown dynamic value. However, since it is within the ETL space, the corresponding transformation has been determined prior to treatment so the tumor's position can be updated during the treatment simultaneously. Equation (2) above is valid as long as the pupil's coordinate system definition in the ETL space remains the same between pre- and intra-treatment, which may imply that the relationship between the camera holder and the patient's head, $T_{ETLCT2\text{-}To\text{-}HeadCT2}$, is unchanged.

Figure 8A:
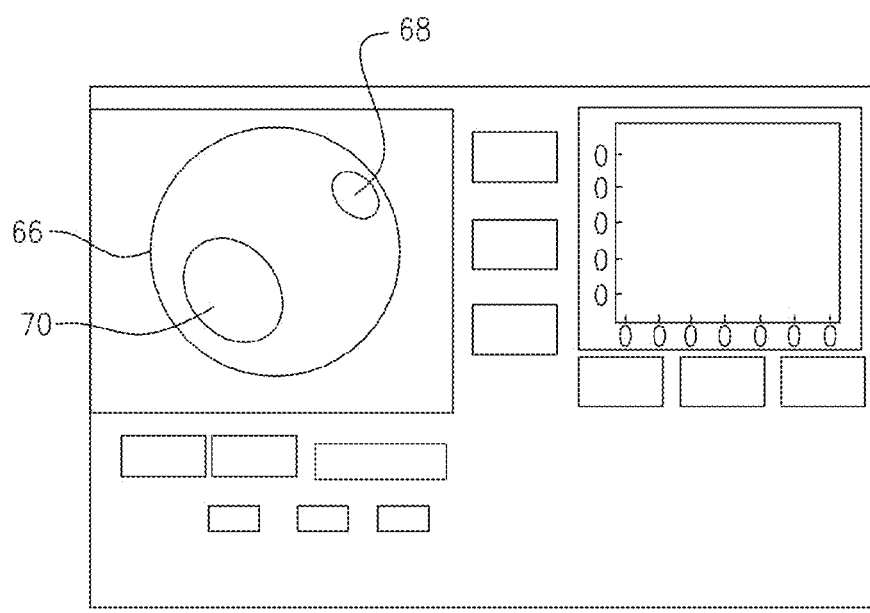
FIG. 8A shows a schematic view of a screenshot of a software simulation in which a virtual eyeball is rotating in 3D space.

A software simulation may be conducted by rotating a virtual eyeball 66 in 3D space (as shown in the schematic view of a screenshot in FIG. 8A) and estimating the difference between the mass centers of the "defined" tumor 68 (represented in FIG. 8A as the small circular area on the left side of the virtual eyeball 66) and the predicted tumor by tracking the center of the pupil (represented in FIG. 8A as the larger circular area on the left side of the virtual eyeball 66). The error caused by mistracking the pupil may be very limited under the ETL's simulation 256×256 window. Mistracking tens of pixels includes only sub-millimeter error. For example, 21 pixels in ETL vs. 0.5 mm in CT (for example, as shown by the non-limiting data in FIG. 8B). In fact, ETL's tracking accuracy is always within 3 pixels (error <0.1 mm). This simulation may ensure the reliability of the tracking device.

Figures 8B, 9:
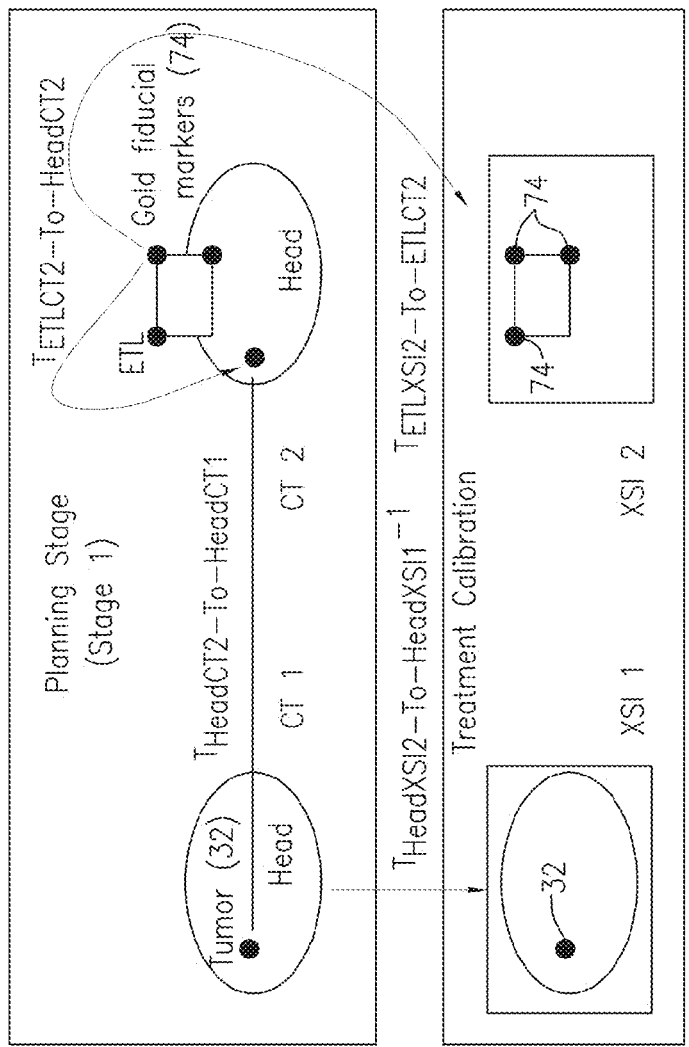
FIG. 8B shows an exemplary error analysis matrix for ETL tracking accuracy.
FIG. 9 shows a schematic representation of camera justification relating to a planning stage and a treatment stage.

It may be desirable to ensure that the camera 52 is mounted at the same position at the planning stage (Stage 1) and the treatment stage (Stage 2). To this end, one or more (for example, three) gold markers or seeds 74 may be embedded on the camera holder 54, 62 as fiducial markers (as shown schematically in FIG. 9). The gold markers 74 may be scanned during CT2 to obtain transformation $T_{ETLCT2\text{-}To\text{-}HeadCT2}$. When the patient 18 is placed in the treatment position, an intra-treatment calibration may be required. The x-ray detectors 20 (XSI) may first identify the patient's current position without the ETL device 54, 56 to get transformation $T_{HeadXSI\text{-}To\text{-}HeadCT1}$. Next, the ETL device 54, 56 with camera 52 may be mounted on the patient 18 and the x-ray detectors 20 (XSI) may be allowed to examine the gold markers 74 to identify the holder's position. By comparing the holder's current position with its position in the CT2 scan, the transformation $T_{ETLXSI2\text{-}To\text{-}ETLCT2}$ may be determined. Since the standalone ETL device 56 (for example, as shown in FIG. 6) may have a rigid translation relation to the CT scan couch and treatment couch, this approach may ensure the device's position is the same during both the planning stage and the treatment stage. FIG. 9 shows this system integration and justification procedure. The transformation system can be simplified by eliminating $T_{HeadCT2\text{-}To\text{-}HeadCT1}$ if the camera is located in such a position that presents no interference with skull stereotactic imaging.

Another means for guaranteeing the same device 54, 56 position may be to use the camera's 52 zoom-out function (with accessory parts from the ETL system) to digitize the patient's partial face. Because the zoom-out factor can be digitally recorded, using the same zoom-out factor at the treatment stage may allow the same position to be found using translation by comparing digitized images based on the image fusion technique.

D. Software Simulation and Hardware Integration

The novel tracking software may be developed under a simulation environment. A human eyeball's digital data set may be imported from, for example, the National Institutes of Health's (NIH's) VISIBLE HUMAN PROJECT®. Using graphical tools, the size and location of a melanoma may be artificially defined. Then, data may be loaded onto a simulation platform, which may have the capability to simulate 3D motion, imaging construction (CT, MRI, and PET), and image processing. By rotating the eyeball data set in 3D space and projecting the pupil's position to 2D space with various scaling factors, the transformations and their accuracies may be derived. The derivation may serve as the foundation for system integration in a real setting. Error analysis under the simulation environment for all parameters may be investigated to ensure system integrity. This may be referred to the first goal, or "Aim 1." The software may be located on a computer 24 having a processor 46, and the processor 46 may be programmable to execute one or more algorithms of the software. For example, the processor 46 may be programmed or programmable to process images and data, to correlate one or more images and data to other images and data and/or predetermined thresholds, and complete one or more transformations discussed herein, such as those according to Equations (1) and (2).

Upon completion of the hardware integration between the ETL pupil tracking system and the CYBERKNIFE system, an eyeball motion phantom 78 may be used to validate communication between all sub-systems. This may be referred to as the second goal, or "Aim 2." The updated tumor's position or the transformation to reflect the updating may be fed to the CYBERKNIFE's robotic arm controller.

E. System Validation (Aim 3)

Figure 10A:
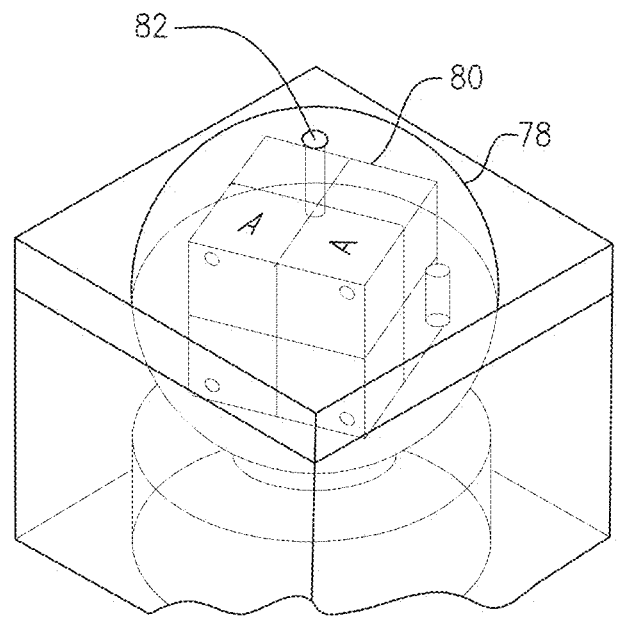
FIG. 10A shows an eyeball phantom.
Figure 10B:
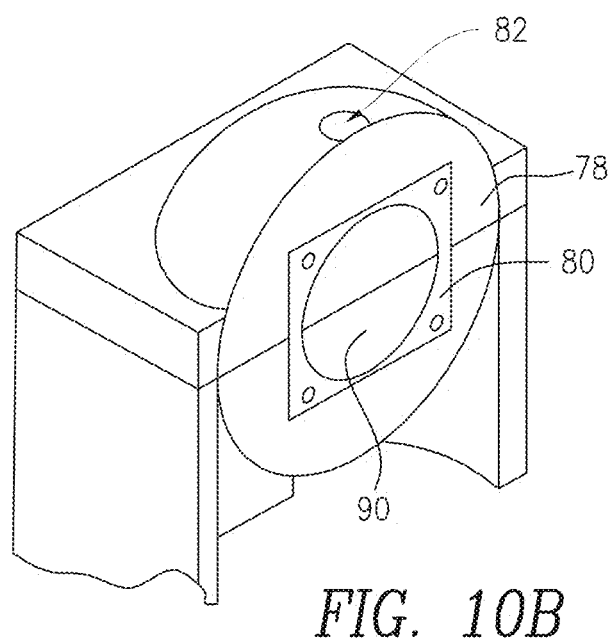
FIG. 10B shows a cross-sectional view of the eyeball phantom of FIG. 10A.
Figure 10C:
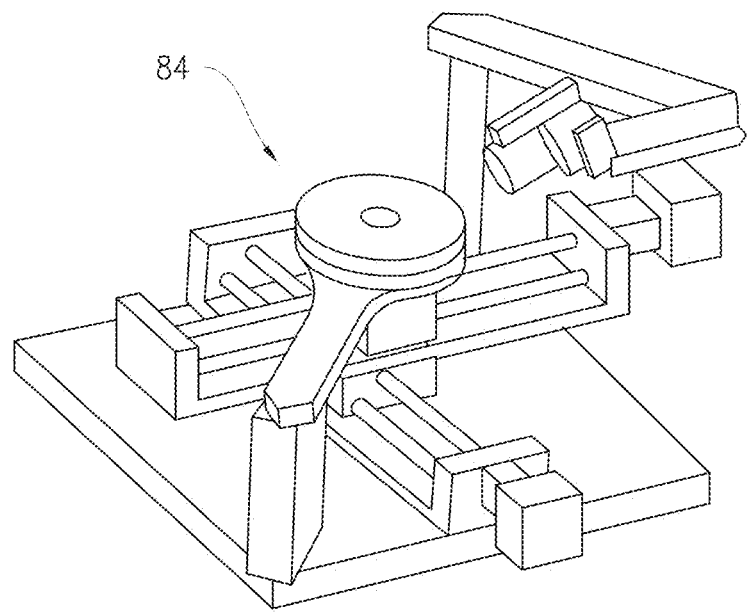
FIG. 10C shows an exemplary x-y stage.

The ultimate goal of this development is to direct the CYBERKNIFE system to deliver a radiation dose to the tumor 32 accurately and precisely. In order to prove the system's efficacy, a motor-driven mechanical phantom 78 may be used to simulate eyeball movement. A radiation dose measurement assembly 80 may be embedded in the eyeball phantom 78 (as shown in FIGS. 10A and 10B). For example, the radiation dose verification assembly 80 may include a cube 82 removably coupled inside the eyeball phantom 78, as shown in FIG. 10A. A simulated pupil 82 may be marked on the eyeball phantom 78, and the pupil's position may then be recorded by the ETL system 50. The bottom of the eyeball phantom 78 may be mechanically connected to an x-y motion stage 84 (such as the non-limiting example shown in FIG. 10C), and movement of the eyeball may correlate to movement of the x-y stage 84, for example, by from translational movement, rotational movement, friction, or other connection. Because the x-y stage 84 may be controlled by programmable step motors, the x-y stage may be programmed in various speeds, locations, and motion patterns to examine the ETL's tracking accuracy. As noted above, the eyeball phantom 78 may house a cubical radiation dose measurement assembly 80 (marked with the letter "A" for "anterior" in FIG. 10A). To conduct validation, the radiation dose measurement assembly 80 may be positioned in any permitted location inside the eyeball phantom 78.

Figure 11A:
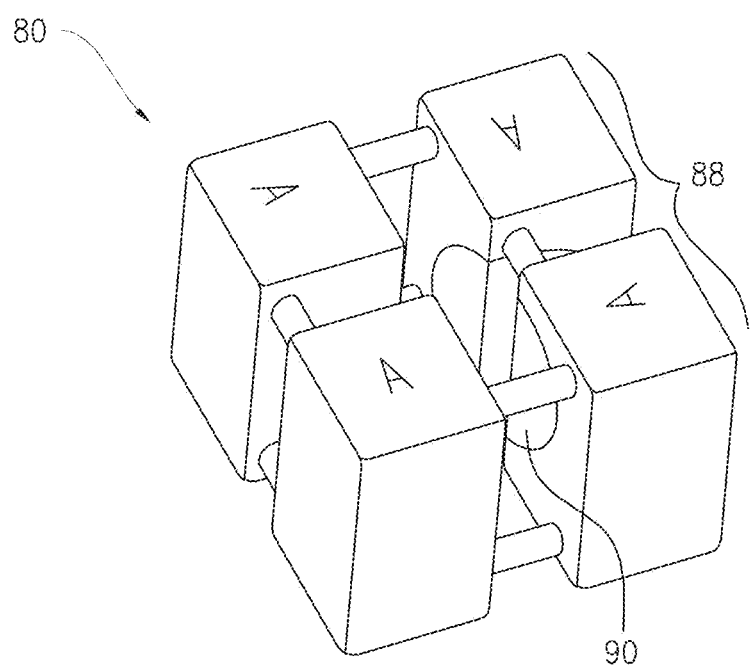
FIGS. 11A-11C show a radiation dose verification assembly.
Figure 11B:
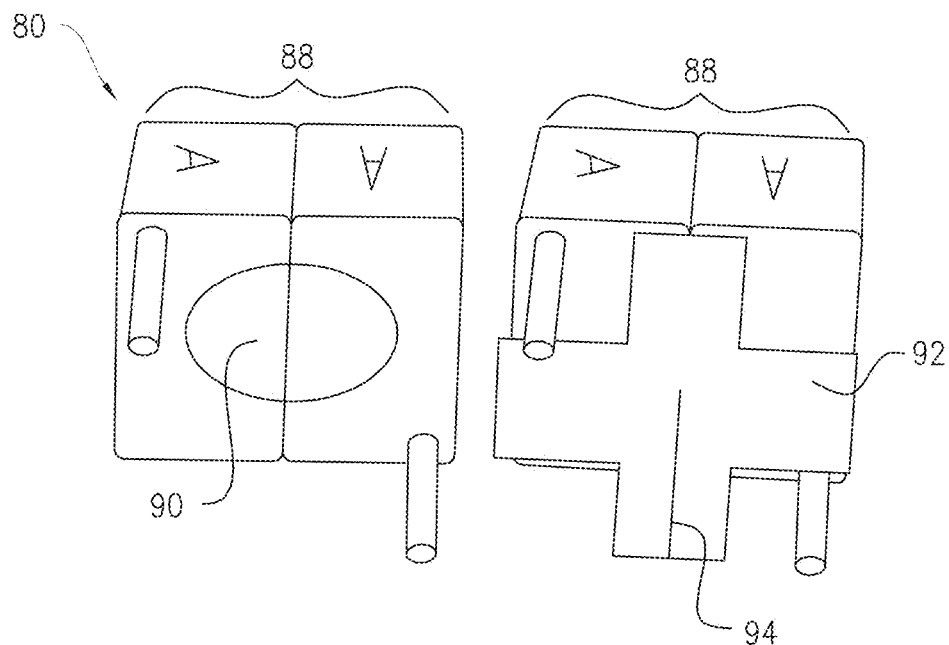
Figure 11C:
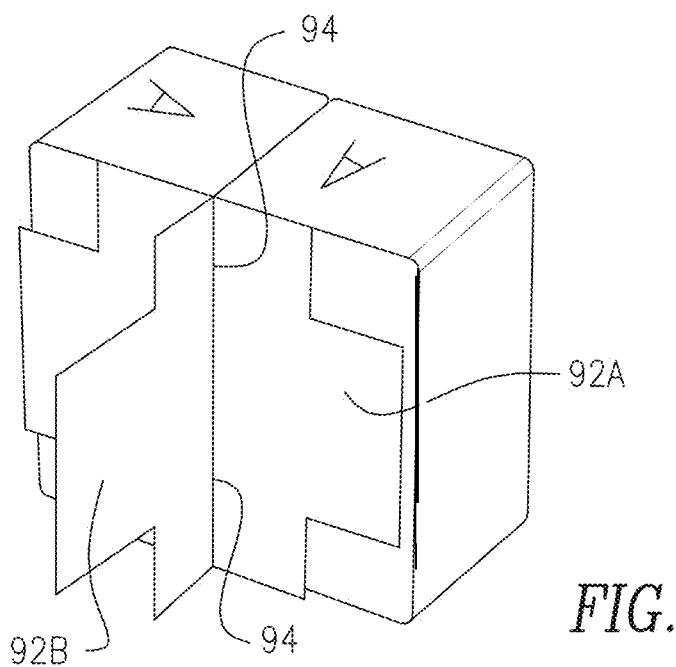

FIGS. 11A and 11B show an exemplary structure of the radiation dose measurement assembly 80. The cubical assembly 80 may include a frame 88 including a plurality (for example, four) components that are removably connectable to each other and that are composed of a tissue-equivalent material. A small sphere or body 90 composed of a material of heavier density may be embedded in the frame 88. Alternatively, at least a portion of the inner portions of each of the frame components may be composed of a heavier density material (as shown in FIGS. 11A and 11B). The heavier density sphere 90 inside the frame 88 may be differentiated under CT and may serve as the simulated tumor 32. The plurality of components may be separated to disassemble the frame 88 into four quadrants, and one or more x-ray films 92 may be perpendicularly inserted into the space between the quadrants. For example, two films 92A, 92B may be used, each of which having a slit 94 that is matable with the slit of the other film (as shown in FIG. 11C). The frame 88 may then be tightly reassembled and inserted into the eyeball phantom 78. The size of the eyeball phantom 78, its range of motion, and the size of the simulated tumor 32 may all be in a 1:1 ratio to those of a human eyeball 34. Tests from CT scan acquisition, treatment planning, to treatment delivery may be conducted using this phantom 78. Integrated with the ETL system and CYBERKNIFE system, by manipulating the validation variables, the phantom 78 may be able to return realistic results for validation. The 3D radiation dose verification may be examined by analyzing two perpendicularly placed x-ray films 92 (FIG. 11C). The dose distribution calculated from the films 92 may be compared to the planned value. Error analysis under the phantom setting may be investigated to demonstrate system efficacy.

F. Results

Figure 12A:
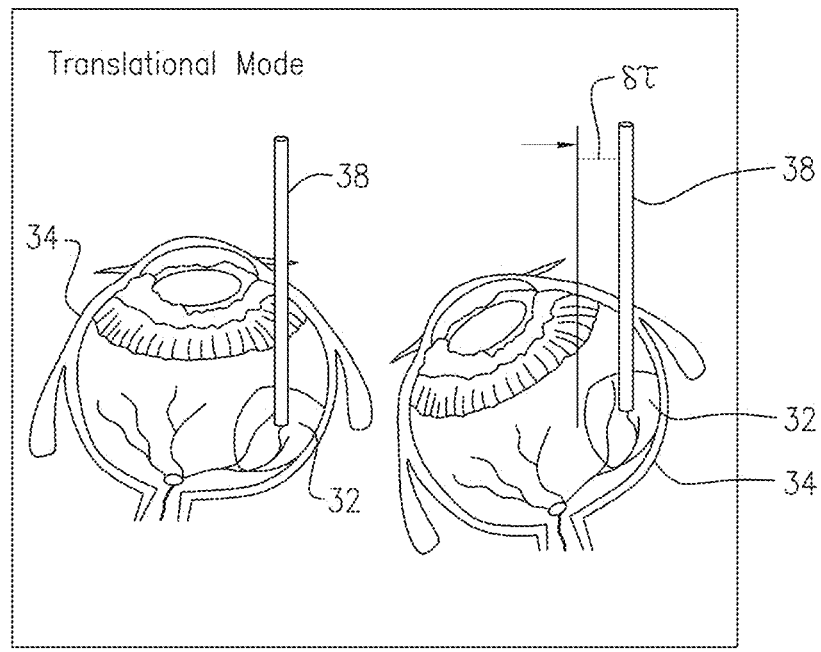
FIG. 12A shows a representation of translational mode adjustment of the CYBERKNIFE system.
Figure 12B:
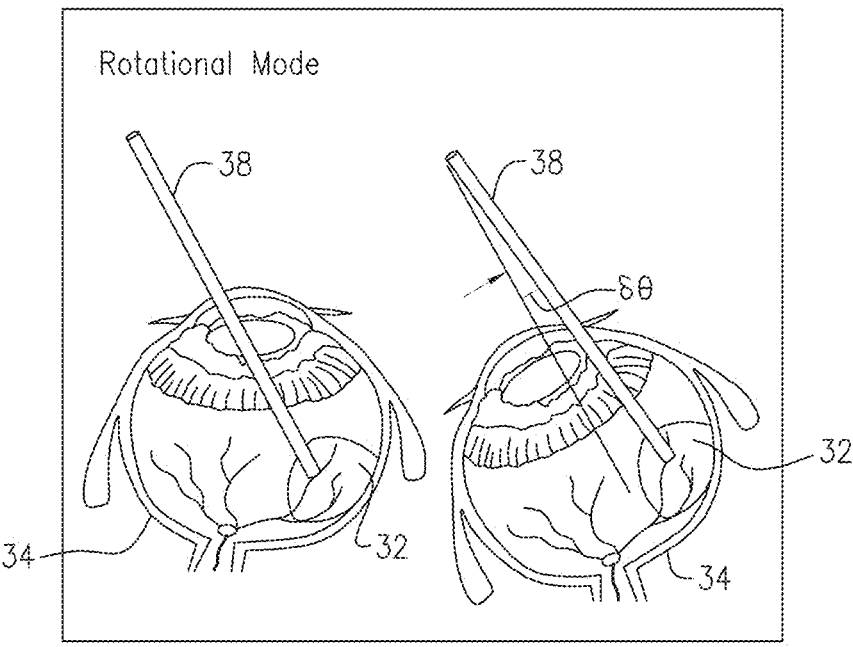
FIG. 12B shows a representation of rotational mode adjustment of the CYBERKNIFE system.
Figure 12C:
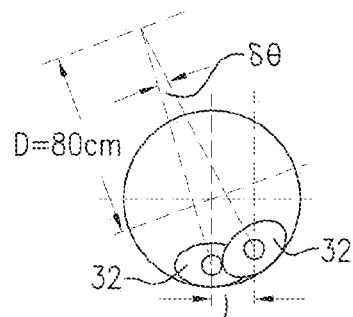
FIG. 12C shows a representation of both translational mode adjustment and rotational mode adjustment of the CYBERKNIFE system.

The designed dynamic pupil tracking system of the present invention may provide the CYBERKNIFE system with accurate and precise information about the tumor's intra-beam position. An optimal isodose line may be produced using one or more of translational adjustment (as shown in FIG. 12A), rational adjustment (as shown in FIG. 12B), or combination thereof of the CYBERKNIFE system. For example, for a 40° saccade from the center, CYBERKNIFE's robot arm translational movement ($\delta T$) is estimated to be approximately 8 mm≈ sin 40°×eyeball radius, and the robot arm rotational movement ($\delta \Theta$) is estimated to be approximately 0.63°≈ $\sin^{-1}(40/360 \times \pi \times$eyeball diameter/80 cm), the distance from the radiation source to the eyeball 34 (as shown in FIG. 12C).

The radiation beams 38 are not guided to follow the eye's saccadic movement. Instead, the eye's (and associated tumor's) position is updated after the saccadic movement. The ETL system 50 may have a sampling frequency of 60 Hz, which may result in the pupil's centroid coordinate being updated about every 20 ms. The subsequent signal decoding and encoding may take about 10 ms. The beam adjustment after every saccadic move (usually about 100 ms) with such a delayed response (20 ms+10 ms=30 ms) is clinically meaningful. Should the delay time (30 ms) turn out unfavorably, such as a saccadic movement during beam delivery, a gated mechanism may be used. The pupil's last position may be recorded and used to determine the current beam's delivery and set up a tolerance range in the ETL space (for example, r=20 pixels, equivalent to 1 mm in the CT space). When the pupil's position is out of the tolerance range, the ETL system 50 may send a signal to the CYBERKNIFE to pause the delivery of radiation. Because the ETL tracking is faster than the saccadic move, the detected and triggering signal will take effect. Using a 120 Hz or 240 Hz ETL system may be desirable.

Figure 13:
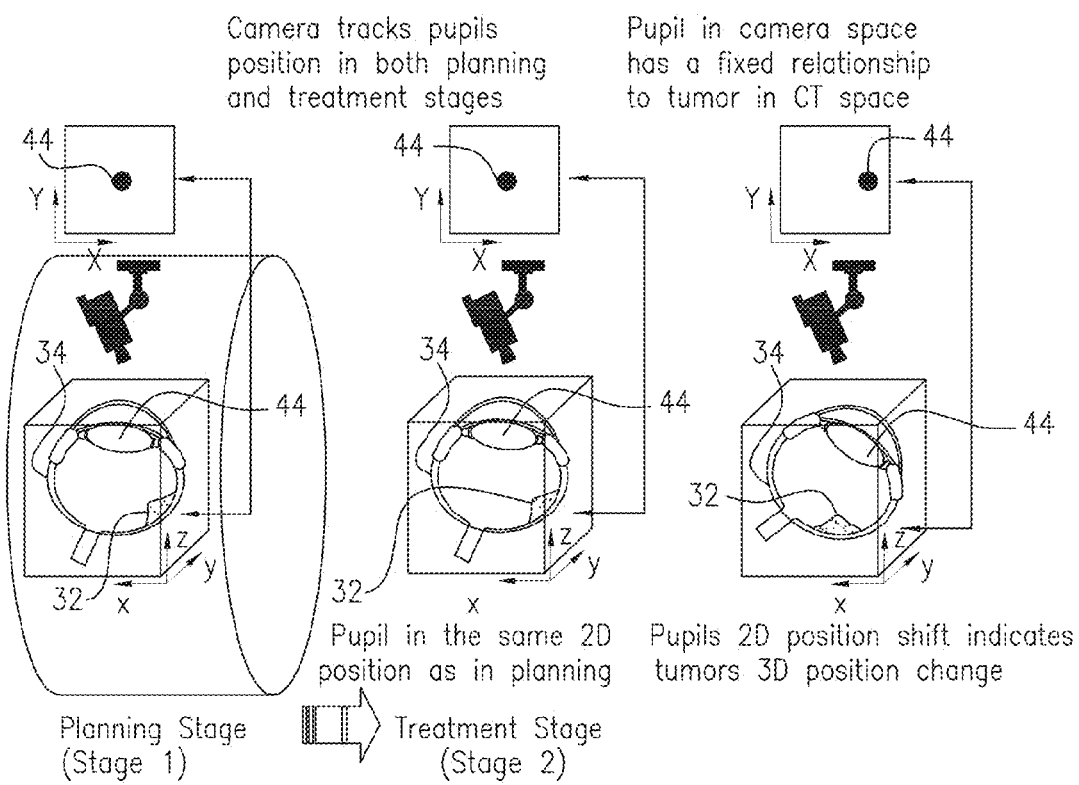
FIG. 13 shows a representation of the planning stage and treatment stage, with eyeball movement, using a system in accordance with the present invention.

FIG. 13 shows a representation of the planning stage (Stage 1) and treatment stage (Stage 2), with eyeball movement, using a system in accordance with the present invention. In contrast to the current CYBERKNIFE system, the system of the present invention allows for intra-beam eye tracking (and therefore, tracking of the tumor 32), even during random and unpredictable eye movement. In the planning stage, the CT scan to localize the tumor's 3D position may remain the same with the pupil 44 in the neutral position by asking the patient to look straight ahead. Additional sets of CT scans (for example, four sets) may be acquired by asking the patient to look to the extreme up, the extreme down, the extreme left, the extreme right, and/or other directions. At the same time, the camera 62 may take pictures of the eye 34. The pupil's 2D coordinates can be identified on the "camera space." These 2D coordinates may then be correlated with the tumor's 3D positions based on captured 2D images of the eye and 3D CT data sets. By interpolation or analytical manipulation (for example, as performed by the one or more processors 46), the relationship between the pupil's 2D coordinates and tumor's 3D positions may be established. In the treatment stage, the same camera 62 with the same mounting position with respect to the patient may be under the CYBERKNIFE. Since the XSI system may assure the patient's same position between the planning stage and the treatment stage, the pupil's coordinates tracked by the camera may dynamically update the tumor's position between radiation beams.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A system for non-invasively treating ocular melanoma, the system comprising:
a CT imaging system, the CT imaging system generating a series of 3D images of a patient's eye and a tumor within the eye;
an optical imaging system, the optical imaging system generating a series of 2D images of a pupil of the patient's eye;
a processor in communication with the CT imaging system and the optical imaging system programmed to correlate the pupil's 2D images with the tumor's 3D images to determine a location of the tumor relative to the pupil in each of a plurality of pupil locations; and
a robotic arm in communication with the processor and configured to direct radiation beams toward the tumor, the direction of the beams being based at least in part on the correlations by the processor.

2. The system of claim 1, wherein the correlation between the pupil's 2D images and the tumor's 3D images is performed by the processor according to the equation:

$$T_i(S) = A(P_i(Se))T_0(S)$$

where:
$T_i(S)$ is the tumor's position within the patient's skull coordinate system;
$T_0(S)$ is an initial position of the tumor within the patient's skull coordinate system;
$P_i(Se)$ is the pupil's position within the patient's eye coordinate system;
A is a transformation that is a function of $P_i(Se)$.

3. The system of claim 2, wherein the initial position of the tumor is the position of the tumor when the eye is in a neutral position.

4. The system of claim 2, wherein the transformation A is an affine transformation.

5. The system of claim 4, wherein the affine transformation is a 3×4 affine transformation.

6. The system of claim 1, further comprising an x-ray imaging system.

7. The system of claim 6, wherein a new location of the tumor relative to the pupil when the eye moves is determined by the processor according to the equation:

$$T_{updated} = T_{current}(S) \times T_{HeadCT2\text{-}To\text{-}HeadCT1} \times T^{-1}_{HeadXSI\text{-}To\text{-}HeadCT1}$$

$$= A(P_{current}(Se))T_0(S) \times T_{HeadCT2\text{-}To\text{-}HeadCT1} \times T^{-1}_{HeadXSI\text{-}To\text{-}HeadCT1}$$

where:
$T_{updated}$ is the tumor's new position of the tumor relative to the pupil;
$T_{current}(S)$ is tumor's new position within the patient's skull coordinate system;
$T_{HeadCT2\text{-}To\text{-}HeadCT1}$ is a transformation based on a change in position of the patient's head between a second series of 3D images by the CT system and a first series of 3D images by the CT system;
$T_{HeadXSI\text{-}To\text{-}HeadCT1}$ is a transformation based on a change in position of the patient's head between a position in an x-ray image of the patient's head by the x-ray imaging system and the position of the patient's head in the first series of 3D images by the CT system;
$T_0(S)$ is an initial position of the tumor within the patient's skull coordinate system;
$P_{current}(Se)$ is the pupil's current position within the patient's eye coordinate system; and
A is a transformation that is a function of $P_{current}(Se)$.

8. The system of claim 7, wherein the initial position of the tumor is a position of the tumor when the eye is in a neutral position.

9. The system of claim 1, wherein the robotic arm delivers radiation beams to the tumor a plurality of times during a treatment.

10. The system of claim 9, wherein the correlation between the pupil's 2D images and the tumor's 3D images is performed between the deliveries of sequential radiation beams in order to direct the radiation beams toward the tumor each time the radiation each time the radiation beams are delivered.

11. The system of claim 9, wherein the correlation between the pupil's 2D images and the tumor's 3D images is performed during the delivery of radiation beams.

12. The system of claim 10, wherein the delivery of radiation beams is paused when the correlation determines the tumor's position is a distance from radiation beams that is greater than a threshold distance.

13. The system of claim 11, wherein the threshold distance is 1 mm.

14. A system for non-invasively treating ocular melanoma, the system comprising:
a first imaging system, the first imaging system generating a first 3D image of a patient's eye and a tumor within the eye when the eye is in a first position and generating a second 3D image of the patient's eye and the tumor within the eye when the eye is in a second position;
a second imaging system, the second imaging system generating a first 2D image of a pupil of the patient's eye when the eye is in the first position and generating a second 2D image of the pupil of the patient's eye when the eye is in the second position;
a processor in communication with the first and second imaging systems, the processor being programmed to correlate the first 3D image with the first 2D image and the second 3D image with the second 2D image; and
a robotic arm in communication with the processor and configured to deliver radiation to the tumor when the eye is in the first location and the second location, the location of the tumor being based on the correlations between the 3D images and the 2D images.

15. The system of claim 14, wherein the location of the tumor when the eye is in the second position is determined by the processor by the equation:

$$T_2(S) = A(P_2(Se))T_1(S)$$

where:
$T_2(S)$ is the tumor's position within the patient's skull coordinate system when the eye is in the second position;
$T_1(S)$ is the tumor's position within the patient's skull coordinate system when the eye is in the first position;
$P_2(Se)$ is the pupil's position within the patient's eye coordinate system when the eye is in the second position; and
A is a transformation that is a function of $P_2(Se)$.

16. The system of claim 15, wherein the transformation A is an affine transformation.

17. A method for performing radiosurgery for ocular melanoma, the method comprising:
generating a first 3D image of an eye having a tumor with a first imaging system when the eye is in a first position;
generating a first 2D image of a pupil of the eye with a second imaging system when the eye is in the first position;
correlating the first 3D image to the first 2D image with a computer having a processor;
determining a first 3D location of the tumor with the computer based on the correlation of the first 3D image to the first 2D image;
delivering radiation to the tumor from a treatment device based on the correlation of the first 3D image to the first 2D image;
generating a second 3D image of the eye with the first imaging system when the eye is in a second position;
generating a second 2D image of the eye with the second imaging system when the eye is in a second position;
correlating the second 3D image to the second 2D image with the computer;
determining a second 3D location of the tumor with the computer based on the correlation of the second 3D image to the second 2D image; and
delivering radiation to the tumor from the treatment device based on the correlation of the second 3D image to the second 2D image.

18. The method of claim 17, further comprising:
pausing the delivery of radiation when at least one of the correlation of the first 3D image to the first 2D image and the correlation of the second 3D image to the second 2D image determines the tumor's position is a distance from a radiation delivery site that is greater than a threshold distance.

19. The method of claim 17, wherein the first imaging system is one of a computed tomography system and a magnetic resonance imaging system.

20. The method of claim 17, wherein the determination of the tumor's second location is determined by the computer by the equation:

$$T_2(S) = A(P_2(Se))T_1(S)$$

where:
$T_2(S)$ is the tumor's position within the patient's skull coordinate system when the eye is in the second position;
$T_1(S)$ is the tumor's position within the patient's skull coordinate system when the eye is in the first position;
$P_2(Se)$ is the pupil's position within the patient's eye coordinate system when the eye is in the second position; and
A is a transformation that is a function of $P_2(Se)$.

* * * * *